(12) United States Patent
Kopperschmidt

(10) Patent No.: US 10,940,255 B2
(45) Date of Patent: Mar. 9, 2021

(54) METHOD AND APPARATUS FOR PREPARING A MEDICAL SOLUTION

(71) Applicant: FRESENIUS MEDICAL CARE DEUTSCHLAND GMBH, Bad Homburg (DE)

(72) Inventor: Pascal Kopperschmidt, Dittelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 188 days.

(21) Appl. No.: 15/568,355

(22) PCT Filed: Apr. 15, 2016

(86) PCT No.: PCT/EP2016/000625
§ 371 (c)(1),
(2) Date: Oct. 20, 2017

(87) PCT Pub. No.: WO2016/169642
PCT Pub. Date: Oct. 27, 2016

(65) Prior Publication Data
US 2018/0140762 A1    May 24, 2018

(30) Foreign Application Priority Data

Apr. 22, 2015    (DE) .................... 10 2015 005 142.3

(51) Int. Cl.
*G05D 11/13* (2006.01)
*A61M 1/16* (2006.01)
*A61M 1/28* (2006.01)

(52) U.S. Cl.
CPC ........ *A61M 1/1656* (2013.01); *A61M 1/1607* (2014.02); *A61M 1/1664* (2014.02);
(Continued)

(58) Field of Classification Search
CPC .............. A61M 1/1656; A61M 1/1664; A61M 1/1607; A61M 1/287; A61M 1/605;
(Continued)

(56) References Cited

U.S. PATENT DOCUMENTS

| 6,139,754 A | 10/2000 | Hartranft et al. |
| 2001/0004523 A1* | 6/2001 | Bosetto .................. A61M 1/16 435/4 |
| 2015/0008183 A1 | 1/2015 | Crnkovich et al. |

FOREIGN PATENT DOCUMENTS

| DE | 69213713 | 3/1997 |
| DE | 102012007412 | 10/2013 |

(Continued)

*Primary Examiner* — Hailey K. Do
(74) *Attorney, Agent, or Firm* — Jacobson Holman PLLC

(57) ABSTRACT

The present invention relates to a method for preparing a medical solution from at least one first liquid component and at least one second liquid component, wherein the first component and the second component are conveyed with a respective conveying means to obtain a mixed solution, wherein the conveying means are operated such that a modulation of the concentration of the first and second components takes place and the conductivity or a parameter of the mixed solution correlating with the conductivity is measured at a measurement point, wherein the modulation of the concentrations takes place in a desired state such that no modulation or a specific desired modulation of the measured conductivity or of the parameter correlated with the conductivity occurs. The present invention furthermore relates to an apparatus for preparing a medical solution as well as to a blood treatment device having such an apparatus.

13 Claims, 1 Drawing Sheet

Figure 1:
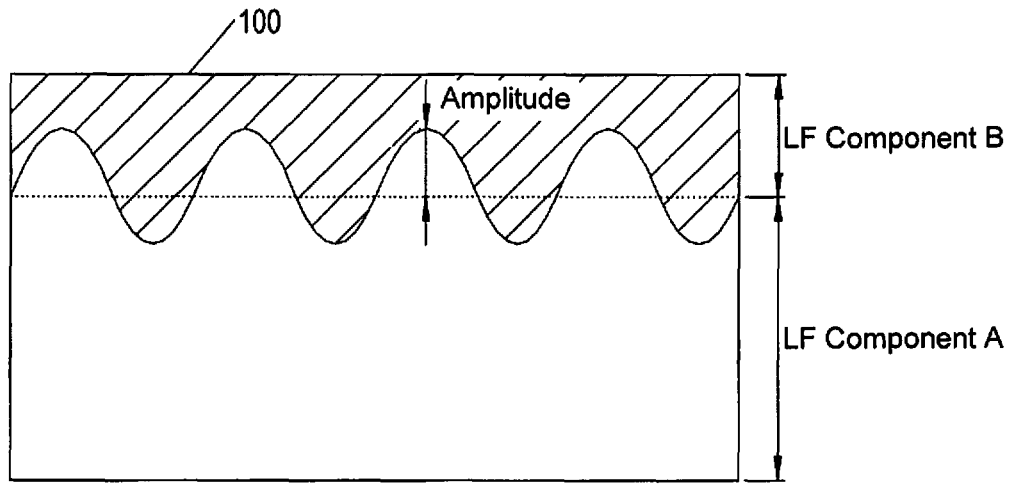

(52) U.S. Cl.
CPC ........... *A61M 1/287* (2013.01); *G05D 11/138* (2013.01); *A61M 2205/3317* (2013.01); *A61M 2205/702* (2013.01)

(58) Field of Classification Search
CPC .... A61M 2205/3317; A61M 2205/702; G05D 11/138; G05D 11/139; B01D 210/647; B01D 604/28; B01D 137/93; B01F 15/00207; B01F 15/00227
See application file for complete search history.

(56) References Cited

FOREIGN PATENT DOCUMENTS

| | | | |
|---|---|---|---|
| DE | 102013218771 | 9/2014 | |
| DE | 102014109369 | 1/2016 | |
| EP | 0160272 | 11/1985 | |
| EP | 2494998 | 9/2012 | |
| EP | 2962711 | 1/2016 | |
| JP | 3319756 B2 * | 9/2002 | .......... A61M 1/1656 |
| WO | WO 2014/121168 | 8/2014 | |
| WO | WO 2014/173747 | 10/2014 | |

\* cited by examiner

METHOD AND APPARATUS FOR PREPARING A MEDICAL SOLUTION

The present invention relates to a method and to an apparatus for preparing a medical solution from at least one first liquid component and from at least one second liquid component, wherein the first component and the second component are each conveyed using at least one conveying means to obtain at least one mixed solution.

It is known from the prior art to prepare dialysis solutions from two components of which the one is an acid concentrate and the other is a base concentrate. The concentration of both components has to be monitored. This takes place in known devices in that a conductivity sensor is provided in conjunction with a temperature measurement to take account of the temperature dependence of the conductivity for each of the components.

The conveying of the components, the of the concentrates, takes place by means of concentrate pumps. If the determined conductivity values differ from desired values, a device alarm takes place.

As stated, the concentrations of the components, also called "partial components" in the following, are typically detected by individual conductivity sensors so that a difference from the respective desired value can be detected independently of the sum concentrations, i.e. of the concentration of the mixed solution containing the components.

It is a disadvantage of this known procedure that a sensor cell is required for each component. Optionally, a further sensor cell for measuring the conductivity of the mixed solution is used as a further protective system so that a comparatively complex structure results overall.

It is the underlying object of the present invention to simplify a method and an apparatus for preparing a medical solution, and in particular a dialysis solution such as is used in hemodialysis, with respect to the prior art.

This object is achieved by a method having the features described below as well as by an apparatus having the features described below.

Provision is made in accordance with the invention that the conveying means are operated such that a modulation of the concentration of the first and second components takes place and that the conductivity of the mixed solution or a parameter of the mixed solution correlated with the conductivity is measured at at least one measurement point, preferably at exactly one measurement point, wherein the modulation of the concentrations in a desired state takes place such that a specific modulation (desired modulation) or no modulation of the mixed solution or of the parameter of the mixed solution correlated with the conductivity occurs.

It is thus the underlying idea of the present invention to convey the components such as the base concentrate and the acid concentrate such that the concentrations of the first component and of the second component in the mixed solution are variable over time.

This modulation of the at least two components can be carried out such that the sum conductivity or the sum concentration correlated therewith, i.e. the conductivity or the concentration of the mixed solution, does not have any modulation, i.e. is constant over time or has a very specific desired modulation.

If is it found in the course of the evaluation of the measured conductivity of the mixed solution or of a parameter correlated therewith such as the sum concentration of the mixed solution that the latter is modulated or differs in its modulation from the determined desired modulation, a conclusion can be drawn on an error state. This can, for example, comprise one of both components beings present in the mixed solution at too high or too low a concentration.

It is particularly advantageous if the modulation of the concentrations of the first and second solutions is carried out such that no temporal fluctuations of the conductivity or of the concentration or of a parameter correlated therewith occur in the mixed solution. If it is then found, differing from this desired state, that the conductivity or a parameter correlated therewith is modulated, i.e. is not constant in time, a conclusion on an error state can be drawn.

Accordingly, an evaluation of the measured value of the mixed solution can be carried out as to whether a modulation of this value is present. If this is the case, a conclusion on an error state can be made.

The same applies accordingly to the case that a very specific desired modulation of the sum concentration, conductivity, etc. of the mixed solution is set which represents the desired state and that it is then found that the actual modulation differs from the determined desired modulation. A conclusion can also be drawn on an error state in this case.

In an advantageous embodiment of the invention, a conclusion can be drawn from the kind of error state on the component whose concentration differs from the expected value. A conclusion is thus not only generally drawn on an error state, i.e. on a state differing from the desired state, but it can rather be determined which of the plurality of components is present in a concentration which differs from the desired value.

It is pointed out at this point that the present invention is not restricted to the use of exactly two solutions for preparing a mixed solution, but that more than two solutions can also be used.

The mixed solution can be the finished medical solution, which can be administered, in particular a dialysis solution, but also a solution which only becomes the finished medical solution, in particular the dialysis solution, after the addition of one or more further substances.

The method in accordance with the invention can be carried out while the patient is not connected to the apparatus for preparing the solution. The case is also covered by the invention that the method is carried out in the sense of an online preparation of the solution while the patient is connected to the apparatus.

The first component can be a base concentrate and the second concentrate can be an acid concentrate. The base concentrate has a pH of >7 and a buffer; the acid concentrate has a pH of <7 and a physiologically compatible acid. One or both components can comprise electrolytes and optionally an osmotic agent.

The present invention allows the monitoring of the physiological properties of the partial components using a single conductivity measurement cell or using only one single sensor which is suitable for measuring the concentration or a parameter correlated therewith or with the conductivity. In addition this cell or the sensor can be used for monitoring the conductivity or the concentration of the mixed solution.

An advantageous embodiment of the invention is thus that no measurement of the conductivity or of a parameter correlated with the conductivity of the first or second component is carried out, but rather only the detection of a parameter, in particular of the conductivity of the mixed solution.

A serial conveying of the components past the measurement point is preferably not provided since, in a preferred embodiment of the invention, a conclusion can be drawn on the component present in error from the measured property of the mixed solution.

Provision is preferably made that a determination can be made from one or more of the following parameters as to which component differs in its concentration from the expected value for this component:

amplitude of the modulation of the measured conductivity of the mixed solution or of the measured parameter of the mixed solution correlated with the conductivity;

mean measured conductivity of the mixed solution or mean value of the measured parameter of the mixed solution correlated with the conductivity; and phase shift of the modulation of the measured conductivity of the mixed solution or of the measured parameter of the mixed solution correlated with the conductivity with respect to the stimulation of the conveying means.

For the last-named alternative, the stimulation of the actuator or of the conveying means, which is preferably configured as a pump, for the component is detected.

In a preferred embodiment of the invention, the modulation of the concentrations of the first and second components takes place in a sinusoidal manner.

The present invention furthermore relates to an apparatus for preparing a medical solution, wherein the apparatus has at least one first conveying means for conveying a first component and at least one second conveying means for conveying a second component and has at least one main line which is in communication with the conveying means such that the components are conveyed into the main line by the conveying means so that at least one mixed solution is created in the main line, wherein at least one, preferably exactly one, sensor is provided in the main line for measuring the conductivity or of a parameter of the mixed solution correlated with the conductivity, and so that the conveying means are configured such that a modulation of the concentrations takes place in a desired state of the apparatus such that a specific desired modulation or no modulation of the measured conductivity of the mixed solution or of the measured parameter of the mixed solution correlated with the conductivity occurs.

The apparatus preferably has at least one evaluation unit which is connected to the sensor and which evaluates the signal detected by the sensor, wherein the evaluation unit is configured such that a conclusion is drawn on an error state when a modulation or a modulation differing from the desired modulation of the measured conductivity of the mixed solution or of the measured parameter of the mixed solution correlated with the conductivity is found.

The evaluation unit can be configured such that it can be determined from the kind of error state which component differs in its concentration from the expected value.

As stated above, exactly one sensor is preferably provided for measuring the conductivity or a parameter of the mixed solution correlated with the conductivity.

Sensors for measuring the individual conductivity or an individual parameter of the first or second components correlated with the conductivity are preferably dispensed with.

The evaluation unit is preferably configured such that a determination is made from the amplitude of the modulation of the measured conductivity or of the parameter correlated with the conductivity and/or from the mean measured conductivity or from the mean value of the parameter correlated with the conductivity and/or from the phase shift of the modulation of the measured conductivity or of the parameter correlated with the conductivity with respect to the stimulation of the conveying means as to which component differs in its concentration from the expected value for this component.

A corresponding sensor or another detection means is provided for the comparison with the modulation of the conveying means and detects this modulation, i.e. the stimulation of the pump or the like.

In a preferred embodiment, the modulation of the concentrations of the first and second components takes place in a sinusoidal manner.

The present invention furthermore relates to a blood treatment apparatus, in particular to a dialysis machine, preferably for carrying out a hemodialysis treatment, wherein the blood treatment apparatus has at least one apparatus in accordance with the invention for preparing the medical solution.

Figure 2:
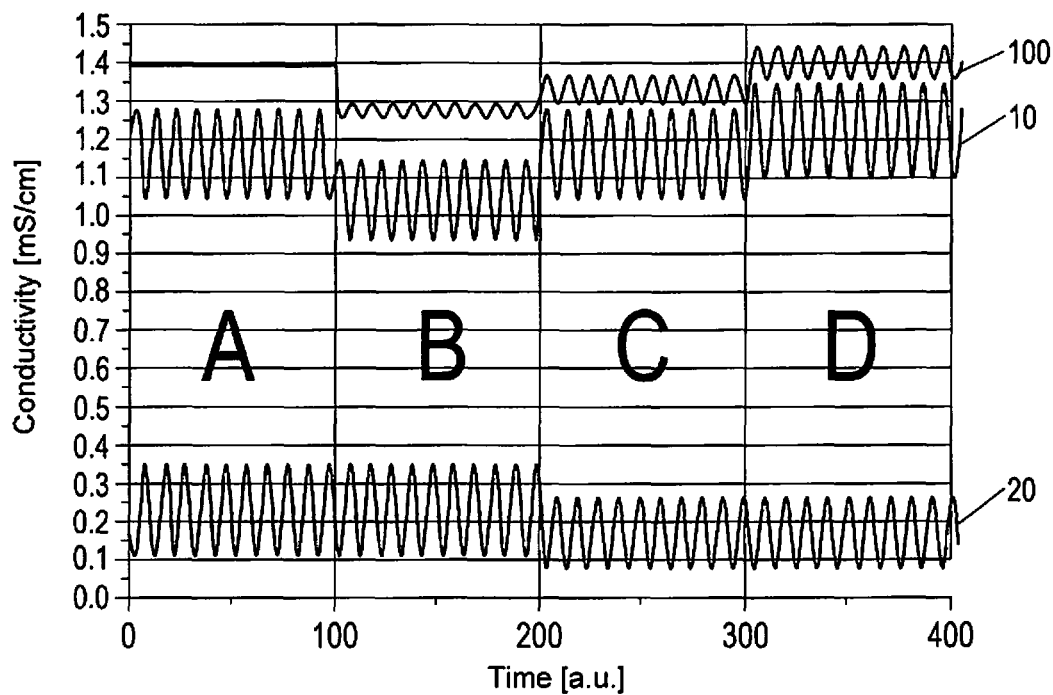
Figure 3:
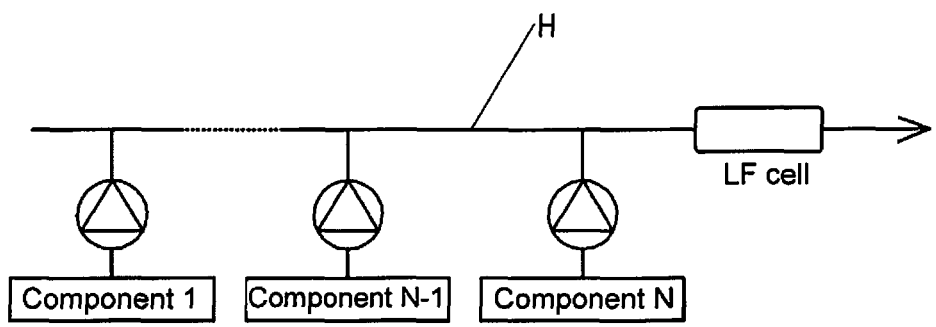

Further details and advantages of the invention will be explained in more detail with reference to an embodiment shown in the drawing. There are shown:

FIG. 1: the sum conductivity of the components A and B and the contribution of the individual conductivities of the components A and B to the sum conductivity;

FIG. 2: the sum conductivity of the components A and B and the contribution of the individual conductivities of the components A and B to the sum conductivity for four different states A to C; and FIG. 3: a schematic view of a multi-component system comprising the components 1 to N with a conductivity measurement cell for measuring the sum conductivity of the mixed solution.

The schematic time development of the sum conductivity 100, i.e. of the conductivity of the mixed solution composed of components A and B can be seen over time from FIG. 1. Furthermore, the time developments of the conductivities of components A and B (LF [=conductivity] component A, LF component B) are shown such that the value for the conductivity of component B (shown in dashed lines) is added to the value of the conductivity of component A so that a sum conductivity 100 constant in time results.

The embodiment relates to the measurement of the conductivity and is also conceivable for the measurement of every other parameter. The invention thus also comprises the measurement of every other parameter of the mixed solution which correlates with the conductivity or with the concentration so that a conclusion can be drawn on the concentration of the components A and/or B or on their ingredients.

It can be seen from FIG. 1 that the pump conveying of the components A and B is modulated such that the sum conductivity 100 of the mixture has no modulation, i.e. is constant in time. The sum concentration, which is correlated with the sum conductivity, is thus constant in time, whereas the concentrations of the components A and B in the mixed solution of both components vary in time.

The conveying of the partial components A and B takes place in the embodiment shown in FIG. 1 phase-shifted by $\pi$ and modulated at a constant phase so that the sum concentration is constant or the sum conductivity has not fluctuations over time.

The amplitude of the concentration fluctuations or conductivity fluctuations, which is shown in FIG. 1, is identical for both components A and B.

If it is assumed that the partial components, i.e. the components A and B, which form the mixed solution or which are optionally present therein in a solvent such as in particular water, have the concentrations $C_A$ and $C_B$ and the individual conductivities or conductivity contributions of the components A and B in the mixed solution are $LF_A(t)$ and $LF_B(Tt)$:

$$LF_A(t)=C_A(1+f_A\sin(\omega t)) \quad (1)$$

$$LF_B(t)=C_B(1+f_B\sin(\omega t)) \quad (2)$$

results for the time development of the conductivities with the relative amplitudes $f_A$ and $f_B$ and with a $\omega$ modulation:

The relative amplitude is the quotient from the absolute amplitude of the concentrate fluctuation and the mean value of the concentration of the components A and B respectively in the mixed solution.

$$C_A f_A = -C_B f_B \quad (3)$$

results from the preferably aimed for freedom of modulations of the sum concentration or of the sum conductivity over time;

and, resolved according to $f_A$:

$$f_A = -f_B(C_B/C_A) \quad (4)$$

If the relative amplitude of the modulation of component B is fixed e.g. to the value 0.5, $$f_A = -0.5(C_B/C_A) = -0.5 f_{AB} \quad (5)$$

furthermore results
where $f_{AB} = C_B/C_A$.

The relative amplitude $f_A$ of component A thus results directly from the aimed for ratio of the concentrations of components B and A in the mixed solution and from the relative amplitude $f_B$ of component B.

The measured sum conductivity, i.e. the conductivity of the mixed solution composed of the individual components A and B, will have the desired expected physiological value in the desired state or will correlate with the expected sum concentration, i.e. with the sum of the concentrations of the individual components A and B. It then $$LF_A(t) + LF_B(t) = C_A(1-0.5(C_B/C_A)\sin(\omega t)) + C_B(1+0.5\sin(\omega t)) = C_A + C_B \quad (6)$$

results for the above-named example with $f_B = 0.5$ from the equations (1), (2) and (5).

The expected values $C_A$ and $C_B$ in the mixed solution are constant in time so that a time consistency also results with respect to the sum conductivity $LF_A(t)+LF_B(t)$.

If the contribution of a component A or B differs from the respective added value, a modulation of the sum conductivity occurs. Depending on which component differs in concentration from the expected value, a specific modulation of the sum conductivity is generated, i.e. the measurement of the sum conductivity generates a characteristic fingerprint. It can thus be determined with reference to the measurement of the sum conductivity which component differs from the expected value.

If it is assumed that component B does not correspond in its concentration in the mixed solution to the expected value $C_B$, but only has the value $C_B'$, which represents a specific fraction $1/\alpha$ of the expected value $C_B$, $$C_B' = 1/\alpha C_B \quad (7)$$

results.

The sum conductivity in this case thus does not have the value resulting from equation (6), but it rather results while taking account of equations (5) and (7) as:

$$LF_A(t) + LF_B(t) = C_A(1 - 0.5(C_B/C_A)\sin(\omega t)) + \quad (8)$$
$$C_B'(1 + 0.5\sin(\omega t))$$
$$= C_A + 1/\alpha C_B + (1/\alpha - 1)C_B/2\sin(\omega t) \quad (9)$$

If thus the component contribution of component B differs by the factor $1/\alpha$ from the expected value, the conductivity of the sum concentration, i.e. of the mixed solution of the two components A and B, in this embodiment thus modulates with the amplitude $(1/\alpha-1)C_B/2$.

The mean sum conductivity in this case corresponds or correlates with $C_A + 1/\alpha C_B$.

If it is assumed that component A does not correspond in its concentration to the expected value $C_A$, but only has the value $C_A'$, which represents a specific fraction $1/\beta$ of the expected value $C_A$, $$C_A' = 1/\beta C_A \quad (10)$$

results.

The sum conductivity in this case thus does not have the value resulting from equation (6), but it rather results while taking account of equations (5) and (10) as:

$$LF_A(t) + LF_B(t) = 1/\beta C_A(1 - 0.5(C_B/C_A)\sin(\omega t)) + \quad (11)$$
$$C_B(1 + 0.5\sin(\omega t))$$
$$= 1/\beta C_A + C_B + (1 - 1/\beta)C_B/2\sin(\omega t) \quad (12)$$

If thus the component contribution of component A differs by the factor $1/\beta$ from the expected value, the conductivity of the sum concentration, i.e. of the mixed solution of the two components A and B, in this embodiment thus modulates with the amplitude $(1-1/\beta) C_B/2$.

The mean sum conductivity in this case corresponds or correlates with $1/\beta\ C_A + C_B$.

The mean conductivity, its amplitude and the phase with respect to the actuator stimulation of the component conveying identify the component whose concentration differs from the expected value.

If the components make different contributions to the sum concentration, a self-compensating difference can also be identified among the components.

FIG. 2 shows the case in state A that the expected values of the contributions A and B have been reached. In this case, the sum conductivity 100 or the sum concentration of the mixed solution shows no modulation, i.e. is constant in time. The reference numerals 10 and 20 characterize the time development of the contributions of the conductivity or of the concentration of the partial components A (reference numeral 10) and B (reference numeral 20) to the conductivity 100 or concentration of the mixed solution.

In the state B, the expected value 20 of component B has been reached, but the actual value of the concentration 10 of component A is below the expected value. The sum conductivity 100 or the sum concentration is below the expected value and is modulated with a phase shift with the different component A.

In the state C, the expected value 10 of component A has been reached, but the actual value of the concentration 20 of component B is below the expected value. The sum conductivity 100 or the sum concentration is below the expected value and is modulated with a phase shift with the differing component B.

In the state D, both expected values of components A and B have not been reached. However, the difference is compensatory, i.e. the sum contribution corresponds to the expected value, i.e. the mean value of the sum conductivity 100 or of the sum concentration corresponds to the expected value.

However, in this case, the sum conductivity 100 or the sum concentration is also modulated, i.e. is not constant in time.

A difference of the concentration contributions of components A and B can thus be performed from the analysis of the modulated sum concentration or sum conductivity.

The phase shift of the modulation of the sum concentration or sum conductivity with respect to the phases of the concentrate conveying pumps results from this analysis.

The mean expected value of the sum concentration or of the sum conductivity indicates an over-conveying or an under-conveying of the differing component, i.e. the mean measured value of the sum conductivity or of the sum concentration indicates an over-conveying or an under-conveying of the differing component.

It can thus, for example, not only be seen from state B in FIG. 2 that component A is present at a concentration differing from the expected value, but also that an under-conveying is present with respect to this component.

FIG. 3 shows a multi-component system with modulated conveying of the concentrations of components 1 to N. All the components are conveyed in a main line H in which the only conductivity measurement cell (LF cell) is located. The respective modulations are characteristic for each component with respect to frequency and phase. This characteristic allows an identification of the contribution of a component differing from the expected value.

A compensatory difference of the components which does not result in a change of the mean sum conductivity or sum concentration can even be determined via the determination of the phase shift of the amplitude of the sum conductivity or of the sum concentration to the phase of the concentrate conveying pump.

In accordance with the invention, only one single conductivity sensor or one single concentration sensor or the like is required for the monitoring of the contributions of the individual components, i.e. of the partial components. The components are added to the main line in which the sensor is located via concentrate pumps conveying with modulation.

Instead of a conductivity sensor or of a concentration sensor, any other sensor can also be used which allows a conclusion on the concentrations or conductivities of the components or on the sum concentration or on the sum conductivity.

The invention claimed is:

1. A method for preparing a medical solution from a first component and a second component, wherein the method comprises the steps of
conveying the first component and the second component as liquids to obtain a mixed solution, characterized in that a modulation of concentrations of the first and second components in the mixed solution takes place, and
measuring conductivity of the mixed solution or a parameter of the mixed solution correlating with the conductivity of the mixed solution at a measurement point,
wherein the modulation of the concentrations of the first and second components takes place in a desired state such that a specific desired modulation or no modulation of the measured conductivity or of the parameter of the mixed solution correlated with the conductivity occurs, characterized in that the modulation of the concentrations of the first and second components takes place in a continuous sinusoidal form.

2. A method in accordance with claim 1, characterized in that the medical solution is a dialysis solution; and/or in that the first component is a base concentrate and the second component is an acid concentrate.

3. A method in accordance with claim 1, characterized in that no serial conveying of the first and second components past the measurement point takes place.

4. A method in accordance with claim 1, characterized in that a determination is made from an amplitude of the modulation of the measured conductivity or of the parameter of the mixed solution correlated with the conductivity of the mixed solution, and/or from a mean measured conductivity of the mixed solution or from a mean value of the parameter of the mixed solution correlated with the conductivity, and/or from a phase shift of the modulation of the measured conductivity of the mixed solution or of the parameter of the mixed solution correlated with the conductivity with respect to stimulation of the conveying as to which component differs in its concentration from an expected concentration.

5. A method in accordance with claim 1, characterized in that an evaluation of the measured conductivity or of the measured parameter of the mixed solution correlated with the conductivity is carried out and a conclusion is drawn on an error state on an occurrence of a difference from the no modulation or on a difference from the desired modulation.

6. A method in accordance with claim 5, characterized in that the conclusion is drawn from the error state on whether the component whose concentration differs from an expected concentration is the first component or the second component.

7. An apparatus for preparing a medical solution, wherein the apparatus has:
a first conveying means for conveying a first component,
a second conveying means for conveying a second component, and
a main line in communication with the first and second conveying means such that the first and second components are conveyed into the main line by the first and second conveying means so that a mixed solution is created in the main line,
characterized in that a sensor is provided in the main line for measuring conductivity or a parameter of the mixed solution correlated with the conductivity, in that the first and second conveying means are configured to effect in a continuous sinusoidal form a modulation of concentrations of the first and second components in the mixed solution in a desired state such that no modulation or a specific desired modulation of the measured conductivity or of the measured parameter of the mixed solution correlated with the conductivity occurs.

8. An apparatus in accordance with claim 7, characterized in that exactly one sensor is provided for measuring the conductivity or the parameter of the mixed solution correlated with the conductivity.

9. An apparatus in accordance with claim 7, characterized in that no sensor is provided for measuring the conductivity or a parameter of the first or second components correlated with the conductivity.

10. A blood treatment device having an apparatus in accordance with claim 7.

11. An apparatus in accordance with claim 7, characterized in that the apparatus has an evaluation unit to which a measurement by the sensor is supplied, wherein the evaluation unit is configured to conclude an error state when a modulation differing from the no modulation is found or when a modulation of the measured conductivity or of the parameter of the mixed solution correlated with the conductivity differing from the specific desired modulation is found.

12. An apparatus in accordance with claim 11, characterized in that the evaluation unit is configured such that it can be determined from the error state which component differs in its concentration in the mixed solution from an expected concentration.

13. An apparatus in accordance with claim 11, characterized in that the evaluation unit is configured such that a determination is made from an amplitude of the modulation of the measured conductivity of the mixed solution or of the parameter of the mixed solution correlated with the conductivity, and/or from a mean measured conductivity of the mixed solution or from a mean value of the parameter of the mixed solution correlated with the conductivity, and/or from a phase shift of the modulation of the measured conductivity of the mixed solution or of the parameter of the mixed solution correlated with the conductivity with respect to stimulation of the first and second conveying means as to which component differs in its concentration from an expected concentration.

\* \* \* \* \*